(12) United States Patent
Ryan, Jr.

(10) Patent No.: US 6,254,530 B1
(45) Date of Patent: *Jul. 3, 2001

(54) SHIELDED ILLUMINATION DEVICE FOR OPHTHALMIC SURGERY AND THE LIKE

(76) Inventor: Edwin H. Ryan, Jr., 752 Goodrich Ave., St. Paul, MN (US) 55105

( * ) Notice: Subject to any disclaimer, the term of this patent is extended or adjusted under 35 U.S.C. 154(b) by 0 days.

This patent is subject to a terminal disclaimer.

(21) Appl. No.: 09/251,111

(22) Filed: Feb. 16, 1999

Related U.S. Application Data

(63) Continuation of application No. 08/957,892, filed on Oct. 27, 1997, now Pat. No. 5,916,149, which is a continuation-in-part of application No. 08/547,930, filed on Oct. 25, 1995, now Pat. No. 5,681,264.

(51) Int. Cl.[7] ................................................. A61B 1/06
(52) U.S. Cl. ..................... 600/177; 600/160; 600/171; 600/249; 606/4; 606/17; 362/572; 362/574
(58) Field of Search ........................... 600/104, 160, 600/171, 176, 177, 181–183, 249; 606/4, 15–17, 161; 362/572, 574

(56) References Cited

U.S. PATENT DOCUMENTS

| | | |
|---|---|---|
| 4,566,438 | 1/1986 | Liese et al. . |
| 5,098,438 | 3/1992 | Siepser . |
| 5,201,730 | 4/1993 | Easley et al. . |
| 5,335,648 | 8/1994 | Kozawa et al. . |
| 5,351,168 | 9/1994 | Easley . |
| 5,352,221 | 10/1994 | Fumich . |
| 5,431,646 | 7/1995 | Vassiliadis et al. . |
| 5,536,234 | 7/1996 | Newman . |
| 5,554,155 | 9/1996 | Awh et al. . |
| 5,667,473 | 9/1997 | Finn et al. . |
| 5,681,262 | 10/1997 | Isse . |
| 5,681,264 | 10/1997 | Ryan, Jr. . |

*Primary Examiner*—John Mulcahy
(74) *Attorney, Agent, or Firm*—Jeffrey S. Schira

(57) ABSTRACT

A illuminated surgical instrument (11) includes an optical fiber (21) with a proximal end and a distal end, a connector (15) disposed at the proximal end of the optical fiber, and a handpiece (13) disposed generally at the distal end of the optical fiber. The handpiece has a handpiece body and a needle (25) extending distally from the handpiece body, the optical fiber (21) extending generally through the handpiece and extending slightly past the distal end of the needle (25). The handpiece (13) is suitable for one-handed operation by a human user, and the needle (25) is of a size suitable for insertion into a human eye. The instrument (11) includes structures at the distal end of the optical fiber (21) for dispersing light passing from an illumination source through the cable to broaden the area on which light impinges, and a shield (47) disposed proximally of a portion of the dispersing structure to prevent light from impinging upon a predetermined area. The predetermined shielded area is disposed proximal the needle (25) and spaced transversely therefrom. A surgical tool disposed adjacent the shield (47) is configured to operate within the area upon which light from the dispersing structure impinges. The surgical tool may include a aspirating/irrigating surgical pic (41), a surgical probe (49), a knife (53), or other surgical tool adapted for insertion into a cavity in the human body such as the interior of a human eye.

12 Claims, 3 Drawing Sheets

SHIELDED ILLUMINATION DEVICE FOR
OPHTHALMIC SURGERY AND THE LIKE

CROSS-REFERENCE TO RELATED APPLICATIONS

This application is a continuation of U.S. patent application Ser. No. 08/957,892, filed Oct. 27, 1997, now U.S. Pat. No. 5,916,149 a continuation-in-part of U.S. patent application Ser. No. 08/547,930, filed Oct. 25, 1995, now U.S. Pat. No. 5,681,264.

STATEMENT REGARDING FEDERALLY SPONSORED RESEARCH OR DEVELOPMENT

Not Applicable.

BACKGROUND OF THE INVENTION

This invention relates to surgery and more particularly relates to illumination devices particularly suited for ophthalmic surgery and the like.

It is known that ophthalmic surgery (and other types of surgery such as laparoscopic and arthroscopic surgery) as well as various procedures such as endoscopy typically require an illumination probe or device which provides illumination for the area under treatment. To provide the best possible visualization for the physician/user of the device, it is preferred that the output of the illumination device be broadband (simulating sunlight to some degree), that the device itself be rather small (so as to not interfere with other instruments being used in the procedure, for example), that the device illuminate a relatively large area at one time, that the light output over the illuminated area be fairly uniform (eliminating dark spots, excessively bright spots, etc.) and not project back towards the operator so as to cause glare that interferes with viewing.

Often the illumination is transmitted from an illumination source (disposed at some distance from the patient) through an optical fiber cable to a handpiece which is manipulated by the physician/user or an assistant to provide illuminating light on the desired area. Optical fiber cables do a good job of providing broad spectrum light from a suitable illumination source, but the light output of optical fibers could be improved. For example, the numerical aperture of optical fibers are typically rather small, with the result that the field of illumination for these devices is smaller than could be desired. Moreover, these devices are most often used in liquids (saline solutions and the like) which further reduces the field of illumination. A narrow field of illumination is adequate for conventional ophthalmic surgical viewing systems, but recently viewing systems have been developed which give the surgeon a more panoramic view of the eye, and require greater dispersion of light to illuminate this larger area. To more uniformly disperse the illumination, lenses have been used as the end of the optical fiber to spread the light. Moreover, at least one device (manufactured by Trek Medical) has been proposed to spread the light by changing the distal configuration of the optical fiber itself from the standard blunt shape to a cone shape. Infinitech, Inc., licensee of the present invention, has also developed a distal configuration of the optical fiber (shown in U.S. Pat. No. 5,351,168) which is believed to address the problem of dispersing the light in a superior manner.

All these devices could be improved however. For example, it has been found that the wide angle illumination devices such as those described above result in light from the illumination probe being transmitted directly into the surgeon's eyes. This, of course, is undesirable and somewhat defeats the purpose of having a wide angle illumination device. This problem makes fine structures adjacent to the probe (e.g. vitreous fibers) quite difficult to see. In addition, glare from the probe becomes increasingly problematic in a gas-filled eye or with poor media. What would be preferred in some instances is a wide angle illumination device which provides means for protecting the surgeon's eyes from direct illumination so as to not affect the surgeon's view of the surgical area.

BRIEF SUMMARY OF THE INVENTION

Among the several objects and features of the present invention may be noted the provision of an improved illumination and surgical device which is especially suited for ophthalmic, laparoscopic, or arthroscopic surgery and endoscopy and the like.

Another object is the provision of such an illumination and surgical device which provides an improved field of illumination while at the same time allowing the surgeon's eyes to be protected from direct illumination.

A third object is the provision of such an illumination and surgical device which is readily controllable by the surgeon.

A fourth object is the provision of such an illumination and surgical device which is reliable, yet relatively simple to manufacture.

Other objects and features will be in part apparent and in part pointed out hereinafter.

Briefly, an illumination and surgical device for ophthalmic surgery and the like includes an optical fiber having a proximal end and a distal end and a connector disposed at the proximal end of the optical fiber. The connector is adapted for connection to a source of illumination and for holding the proximal end of the optical fiber in position to accept light from the illumination source. A handpiece is disposed generally at the distal end of the optical fiber and has a handpiece body and a surgical tool extending distally from the handpiece body. The optical fiber extends generally through the handpiece. It is preferred that the handpiece be of a size suitable for one-handed operation by a human user, and that the surgical tool be of a size suitable for insertion into a cavity in the human body such as the interior of a human eye. A structure is disposed at the distal end of the optical fiber for dispersing light passing from the illumination source through the cable to broaden the area on which the light impinges. A shield is provided proximally of at least a portion of the dispersing means to prevent light from impinging upon a predetermined area, which predetermined area is disposed proximal the needle and spaced transversely therefrom.

The foregoing and other objects, features, and advantages of the invention as well as presently preferred embodiments thereof will become more apparent from the reading of the following description in connection with the accompanying drawings.

BRIEF DESCRIPTION OF THE SEVERAL VIEWS OF THE DRAWINGS

In the accompanying drawings which form part of the specification.

Corresponding reference numerals indicate corresponding parts throughout the several figures of the drawings.

DESCRIPTION OF THE PREFERRED EMBODIMENT

Figure 1:
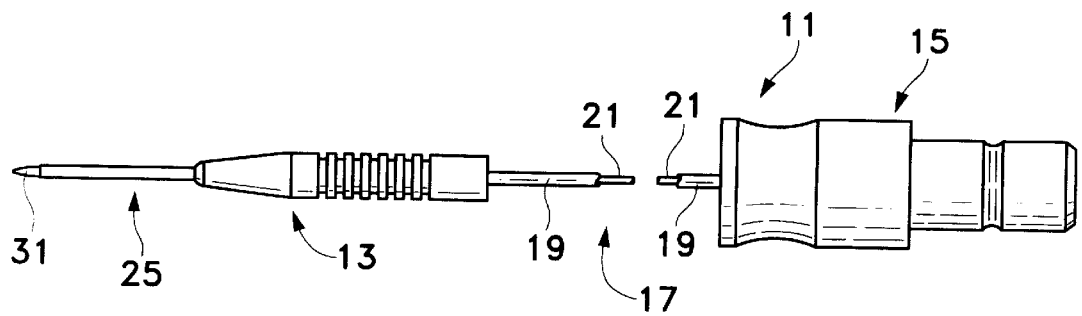
FIG. 1 is a side elevation of the illumination device disclosed in the parent application.

The following detailed description illustrates the invention by way of example and not by way of limitation. The description will clearly enable one skilled in the art to make and use the invention, describes several embodiments, adaptations, variations, alternatives, and uses of the invention, including what is presently believed to be best mode of carrying out the invention.

Turning to the drawings, an illumination device 11 of the present invention includes a handpiece 13, an illumination light source connector 15, and an optical fiber cable 17. The optical fiber cable 17 typically includes a protective sheath 19 covering either a single or multiple optical fibers 21. A single optical fiber composed of plastic is preferred, although multiple optical fibers or fibers composed of glass could also be used in the present invention.

A hollow metal probe needle 25 is connected to the body of the handpiece 13 and extends distally therefrom. The body of the handpiece 13 is used to manipulate the position of the probe needle 25 to provide illumination passing through the needle to the desired locations during an operation or procedure. For ophthalmic surgery, the probe needle 25 is of a size suitable for insertion into a human eye. Illumination devices for other operations and surgical procedures could differ in size.

As can be readily seen in FIG. 1, the optical fiber cable 17 terminates proximally in illumination connector 15 in such a manner that it is exposed to illuminating light from the light source. The optical cable extends for any desired length (such an six feet or so) and terminates distally adjacent the probe needle 25. The optical fiber cable 17 thereby forms an optical path for the illuminating light from the light source to an eye (or other body part or organ).

Figure 2:
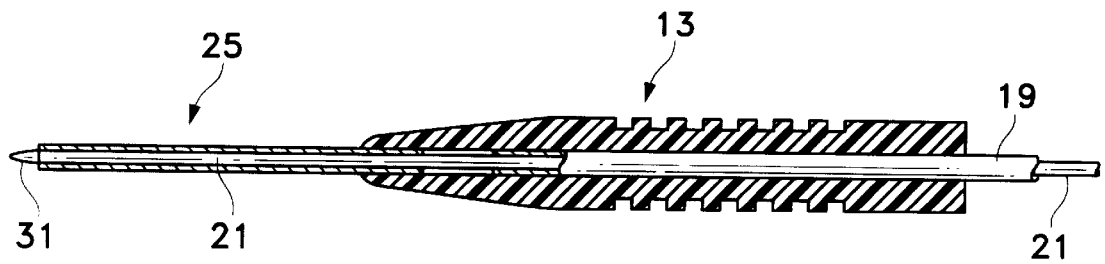
FIG. 2 is an enlarged sectional view of the distal end of the device of FIG. 1.

As can be seen more clearly in FIG. 2, the sheath 19 terminates in the body of the handpiece 13 while the optical fiber 21 itself terminates at the distal end of the probe in a bullet-shaped tip 31. Such a tip is only one of the possible dispersing devices usable in the present invention. Other alternatives are described in the parent application, Ser. No. 08/547,930. Any suitable lens configuration could be used as well. Although the tip 31 is preferably formed on the distal end of optical fiber 21, it may also be formed as a separate part which is suitably secured to the distal end of the probe needle 25. The tip 31 is preferably shaped so as to provide illumination over as wide a field of illumination as possible when the tip is disposed in a location for use. Although the present invention can be used with a wide variety of light dispersing structures, such as those described above and in the parent application, it is described hereinafter in connection with the bullet-shaped tip 31 shown in FIG. 2.

Figure 3:
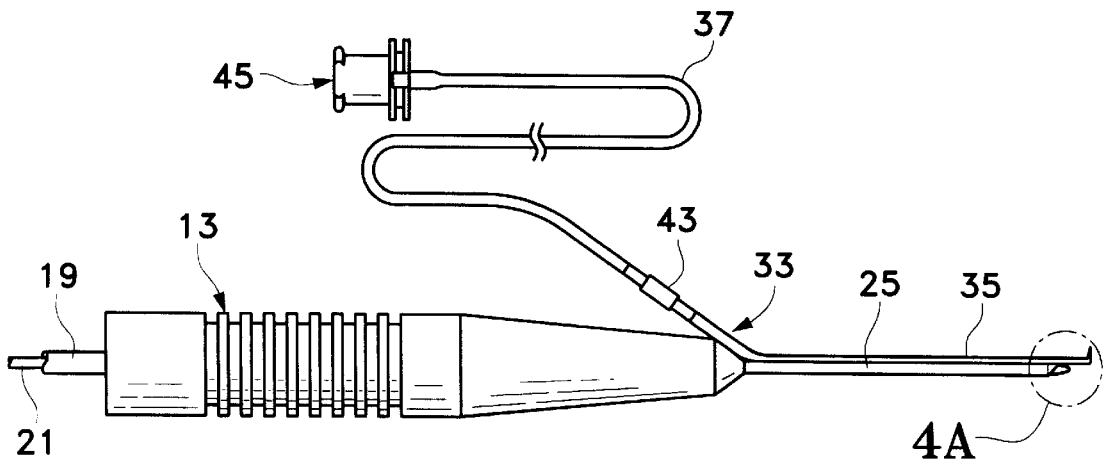
FIG. 3 is an enlarged view of the distal end of one embodiment of the illuminating device of the present invention adapted for use with an aspirating pic.
Figure 4A:
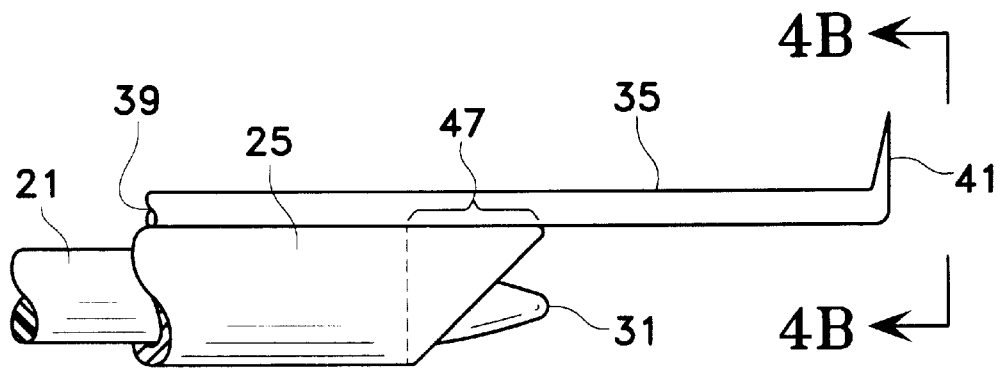
FIG. 4A is an enlarged view the distal region indicated at 4A in FIG. 3.
Figure 4B:
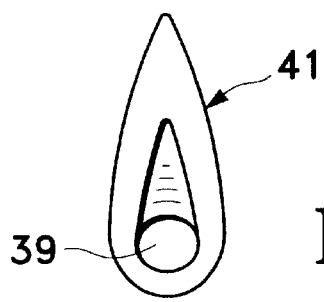
FIG. 4B is an end view of the region indicated at 4B in FIG. 4A.

Referring now to FIG. 3, an embodiment of the present invention including an aspirating pic is shown. The aspirating pic 33 consists of a small diameter rigid tube 35 affixed parallel to the exterior of the probe needle 25, and a flexible suction tube 37 secured to the proximal end of the rigid tube 35. The rigid tube 35 is axially traversed by a fluid pathway 39, and terminates in a surgical pic 41 extending beyond the bullet-shaped tip 31 as best seen in FIG. 4A. The surgical pic 41 is preferably formed by bending and shaping the distal end of the rigid tube 35 perpendicular to, and away from, the axis of the probe needle 25, creating a tear-drop shape best seen in FIG. 4B. One skilled in the art will recognized that the surgical pic 41 may also be formed separately from the rigid tube 35, and then secured thereto by a convention means such as brazing or welding.

The fluid pathway 39 traverses the length of rigid tube 35 and opens at the base of surgical pic 41, allowing fluids or other material to be drawn through tube 35, by suction. During use in ophthalmic surgery, the suction force drawing fluid or other material through the fluid pathway 39 allows the surgical pic 41 to be employed as a tissue manipulator. The tissue (not shown) is drawn against the base of the surgical pic 41, and retained there by the suction forces, allowing the operator to grip and manipulate the tissue.

For use in ophthalmic surgery it is preferred that the surgical pic 41 project approximately 0.020 inches perpendicular to the longitudinal axis of the rigid tube 35. Although the embodiment shown is adapted for use in ophthalmic surgery, it will be understood that the size and shape of the surgical pic 41 may be varied to conform to the specialized needs of different surgical procedures.

The proximal end of the rigid tube 35 is located adjacent to, and apart from, the handpiece 13, and terminates in a connector 43 suitably adapted for connection to the distal end of the flexible suction tube 37, or other flexible piping material. In the embodiment shown, the preferred connector 43 is a short length of silicone tubing press fitted over the proximal end of the rigid tube 35 and the distal end of the flexible suction tube 37, forming a tight seal. The flexible suction tube 37, preferably composed of a silicone material, terminates proximally at an adapter 45 configured for connection to a conventional suction device (not shown). The flexible suction tube 37 extends for any desired length (such as two feet or so) sufficient to allow the operator to manipulate the aspirating pic 33 without interference from the suction device. Those skilled in the art will recognize that the illuminated aspirating pic embodiment of the invention may easily be adapted for use as an illuminated irrigating pic, by delivering an irrigating solution to the distal end of the surgical pic 41 through the flexible suction tube 37 and the fluid pathway 39.

As can be seen in FIG. 4A, the aspirating pic embodiment of the invention further includes a shield 47 disposed at the end of the needle 25, and preferably parallel thereto, adjacent the rigid tube 35. Preferably the shield is an extension of the needle 25 and is formed integrally with the needle as a single piece. This may be accomplished, for example, by suitably beveling the distal end of the needle 25 to provide the wedge shaped shield 47. A bevel angle of approximately 45° has been found to be satisfactory, however, alternate bevels having angles greater or less than 45° may be employed. Similarly, the shield 47 may be composed of a compound bevel having two or more facets, or a curved or radiused bevel. This shield is relatively pointed at its distal end and widens proximally in a smooth manner. It is preferred that any transitions in the shield 47 be smooth to reduce the possibility of unnecessary trauma to the patient. Although the shield 47 is preferably an extension of the needle 25, the shield can be formed in other ways. For example, the shield 47 may be painted directly onto the relevant portion of dispersing element 31.

It is preferred that the tip of the dispersing structure, in this case the bullet tip of the optical fiber, extend distally past the distal end of the shield a predetermined distance such as 0.005" to 0.020". One skilled in the art will recognize that the tip of the dispersing structure may also be positioned flush with the distal end of the shield, or be recessed in the proximal direction from the distal end as required by the various surgical procedures being performed. The preferred extension allows illumination from the optical fiber to illuminate the vast majority of the operative field while shielding the operator from direct illumination. By suitable manipulation of handpiece 13 the operator can always insure that the shielded area includes the operator's eye(s). This embodiment of the invention affords multiple significant functional benefits. The shielding eliminates glare in all viewing situations, which is particularly important and beneficial when the media are poor. Also, the absence of glare allows the surgeon to visualize fine structures (such as the vitreous) adjacent to the surgical pic 41, something that is not possible with present diffuse illumination probes. This property allows the illuminating aspirating pic to be more versatile in that it can be effectively used with both conventional and panoramic viewing systems, something not possible with current illuminated devices.

Figure 5:
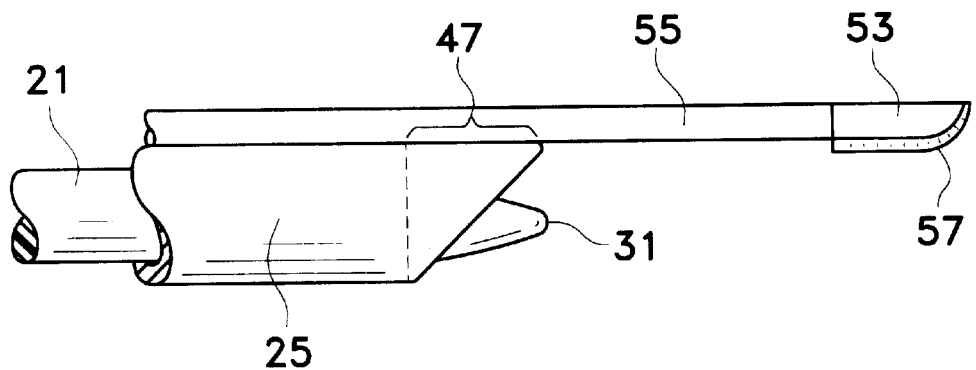
FIG. 5 is an enlarged view similar to FIG. 4A of an alternate embodiment of the illuminating device of the present invention adapted for use with a surgical scalpel.

Referring now to FIG. 5, an alternate embodiment of the present invention including a surgical scalpel is shown. The surgical scalpel 53 is carried on a rigid member 55 secured to the exterior of the needle probe 25, and extending beyond the distal end of the bullet tip 31. The surgical scalpel 53 shown in FIG. 6 includes a single cutting edge 57, however, one skilled in the art will recognized that this alternate embodiment may be adapted with surgical scalpels of various sizes, shapes, and with either single or double cutting edges.

Figure 6A:
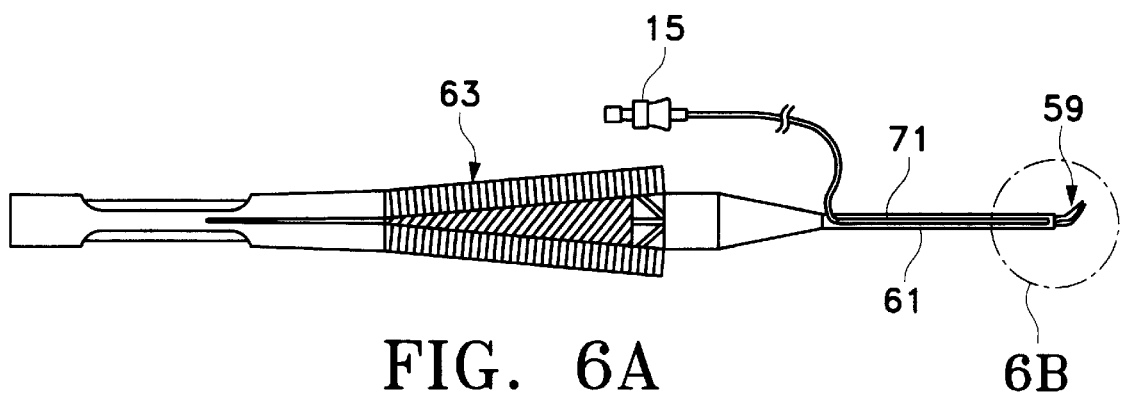
FIG. 6A is an illustration of an alternate embodiment of the illuminated device of the present invention adapted for use with a surgical scissors.
Figure 6B:
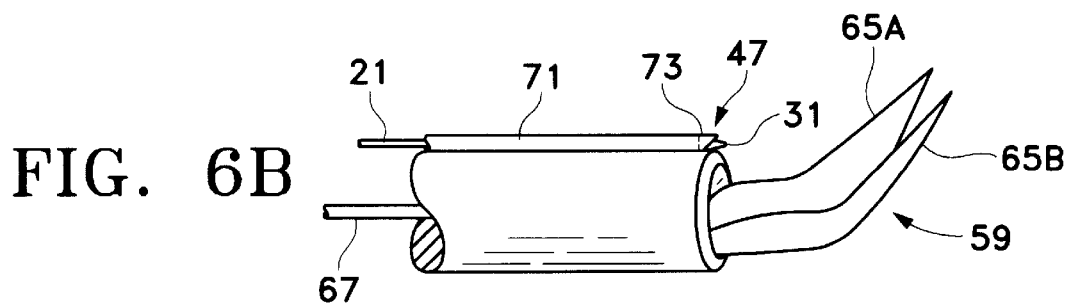
FIG. 6B is an enlarged view of the distal region indicated at 6B in FIG. 6A.
Figure 7A:
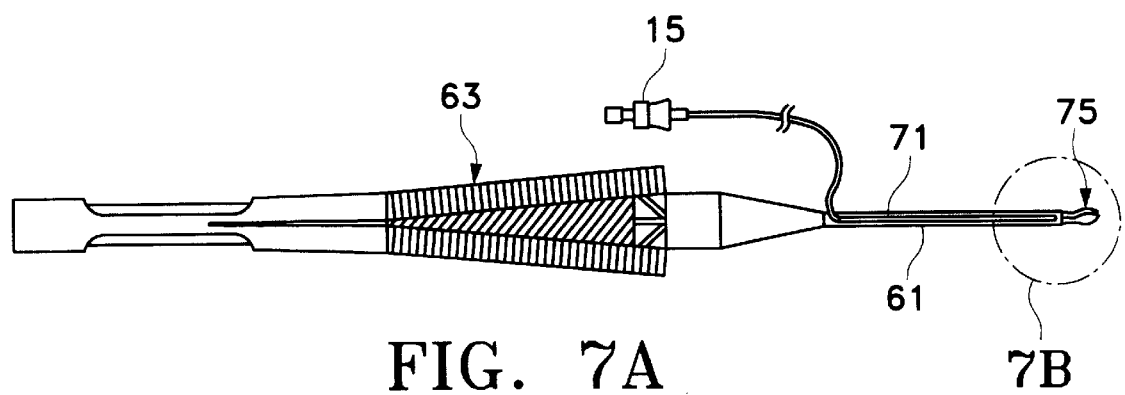
FIG. 7A is an illustration of an alternate embodiment of the illuminated device of the present invention adapted for use with a surgical forceps/retractors.
Figure 7B:
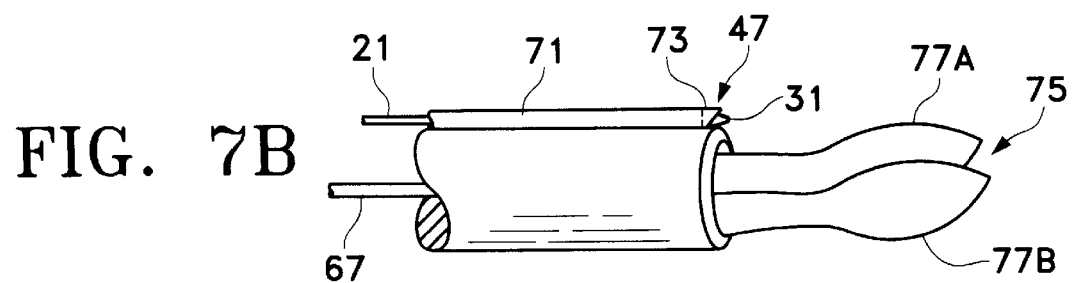
FIG. 7B is an enlarged view of the distal region indicated at 7B in FIG. 7A.

One skilled in the art will recognize that further alternate embodiments are within the scope of the present invention. These may include a variety of other surgical tools, including surgical scissors and surgical forceps/retractors which are configured to operated in the area upon which light dispersed from the bullet tip 31 impinges. FIGS. 6A and 6B illustrates an alternate embodiment of the present invention adapted for use with surgical scissors 59. The surgical scissors 59 include an elongated support shaft 61 with a manipulating grip or handle 63 mounted on a proximal end of the shaft 61, and a pair of scissor blades 65A and 65B disposed on the distal end of the shaft 61 for manipulating tissue. An operator's manipulation of the manipulating grip or hand 63 is conveyed to the scissor blades 65A and 65B by means of an actuating rod or cable 67 which passes through the elongated support shaft 61.

A fiber cannula 71 secured to the exterior of the support shaft 61 removably holds the optical fiber 21 in position adjacent the scissor blades 65A and 65B, allowing illumination to be delivered to the blades. As previously described, the optical fiber terminates proximally in the illumination connector 15, and distally in the bullet-shaped dispersing tip 31. The dispersing tip 31 is held by the fiber cannula 71 adjacent the shield 47 so as to allow light from the dispersing tip 31 to illuminate the operator's field of view while simultaneously shielding the operator from direct illumination. The shield 47 is preferably positioned with the elongated portion 73 of the shield 47 spaced apart from the shaft 61, such that the region shielded from direct illumination corresponds with the position of an operator manipulating the surgical scissors 59.

A similar alternate embodiment adapted for use with surgical forceps/retractors 75 shown in FIG. 8, operates in an identical manner, with a forceps/retractor arms 77A and 77B carried on the elongate support shaft 61 opening and closing in response to movement of the actuating rod or cable 67 controlled by the manipulating grip or hand 63. The fiber cannula 71 incorporating the shield 47 holds the optical fiber 21 such that the dispersing tip 31 illuminates the area surrounding the forceps/retractor arms while simultaneously shielding the operator from direct illumination.

In view of the above, it will be seen that the several objects of the invention are achieved and other advantageous results are obtained. As various changes could be made in the above constructions, including the adaptation of the shield 47 and dispersing tip 31 for use with additional surgical instruments, without departing from the scope of the invention, it is intended that all matter contained in the above description or shown in the accompanying drawings shall be interpreted as illustrative and not in a limiting sense.

What is claimed is:

1. An illuminated surgical instrument for ophthalmic surgery comprising:

an optical fiber having a proximal end and a distal end;

a connector disposed at the proximal end of the optical fiber, said connector being adapted for connection to a source of illumination and for holding the proximal end of the optical fiber in position to accept light from the illumination source;

a handpiece disposed generally at the distal end of the optical fiber, said handpiece having a handpiece body and a needle extending distally from the handpiece body, said optical fiber extending generally through the handpiece, said handpiece being of a size suitable for one-handed operation by a human user, and the needle being of a size suitable for insertion into a cavity in the human body such as the interior of a human eye;

means at the distal end of the optical fiber for dispersing light passing from the illumination source through the cable to broaden the area on which the light impinges;

a shield having a distal end disposed adjacent the dispersing means to prevent light from impinging upon a predetermined area, said predetermined area being disposed proximal to the needle and spaced transversely therefrom, the distal end of the shield being disposed proximally of the distal end of the optical fiber; and a surgical tool disposed adjacent at least a portion of said needle and extending distally beyond said dispersing means, said surgical tool operating in the area on which said light impinges, and being of a size suitable for insertion into a cavity in the human body such as the interior of a human eye.

2. The illuminated surgical instrument as set forth in claim 1 wherein said surgical tool is a surgical pic.

3. The illuminated surgical instrument as set forth in claim 2 wherein said surgical pic is mounted on the distal end of a rigid tube, said rigid tube being affixed to the exterior of said needle, and having a fluid pathway disposed therein, the proximal end of said rigid tube being positioned adjacent to, and apart from, said handpiece.

4. The illuminated surgical instrument as set forth in claim 3 wherein said rigid tube is an aspirating tube, said proximal end of said aspirating tube being adapted for connection to a flexible suction tube.

5. The illuminated surgical instrument as set forth in claim 3 wherein said rigid tube is an irrigation tube, said proximal end of said irrigating tube being adapted for connection to a flexible irrigating tube.

6. The illuminated surgical instrument as set forth in claim 3 wherein said surgical pic extends angularly away from said needle, the distal end of said fluid pathway being disposed in said surgical pic.

7. The illuminated surgical instrument as set forth in claim 6 wherein said surgical pic extends perpendicularly away from said needle.

8. The illuminated surgical instrument as set forth in claim 3 wherein said surgical pic is an extension of said rigid tube.

9. The illuminated surgical instrument as set forth in claim 3 wherein said surgical pic is welded to said rigid tube.

10. The illuminated surgical instrument as set forth in claim 2 wherein said surgical pic has a tear-drop shaped frontal section.

11. The illuminated surgical instrument as set forth in claim 1 wherein said surgical tool is a surgical scalpel.

12. The illuminated surgical instrument as set forth in claim 11 wherein said surgical scalpel is mounted on the distal end of a rigid member affixed to said needle and extending distally from said dispersing means, said surgical scalpel including at least one cutting edge.

* * * * *